US008125225B2

(12) United States Patent
Koretsky et al.

(10) Patent No.: US 8,125,225 B2
(45) Date of Patent: Feb. 28, 2012

(54) TRANSMIT PROFILE CONTROL IN MRI

(75) Inventors: Alan P. Koretsky, Bethesda, MD (US);
Jeff H. Duyn, Garrett Park, MD (US);
Shumin Wang, Bethesda, MD (US);
Hellmut Merkic, Bethesda, MD (US)

(73) Assignee: The United States of America as represented by the Secretary, Department of Health and Human Services, Washington, DC (US)

( * ) Notice: Subject to any disclaimer, the term of this patent is extended or adjusted under 35 U.S.C. 154(b) by 160 days.

(21) Appl. No.: 12/449,514

(22) PCT Filed: Feb. 13, 2008

(86) PCT No.: PCT/US2008/001911
§ 371 (c)(1),
(2), (4) Date: Aug. 12, 2009

(87) PCT Pub. No.: WO2008/100546
PCT Pub. Date: Aug. 21, 2008

(65) Prior Publication Data
US 2010/0164494 A1    Jul. 1, 2010

Related U.S. Application Data

(60) Provisional application No. 60/900,972, filed on Feb. 13, 2007.

(51) Int. Cl.
*G01V 3/00* (2006.01)
(52) U.S. Cl. ........................................ 324/318; 324/309

(58) Field of Classification Search .......... 324/300–322;
600/407–445; 335/296, 297, 299
See application file for complete search history.

(56) References Cited

U.S. PATENT DOCUMENTS

| | | | |
|---|---|---|---|
| 4,617,936 A | 10/1986 | Malko | |
| 4,694,836 A | 9/1987 | Buikman et al. | |
| 4,784,146 A | 11/1988 | Mancuso et al. | |
| 5,063,933 A | 11/1991 | Takahashi | |
| 5,150,710 A | 9/1992 | Hall et al. | |
| 5,296,810 A | 3/1994 | Morich | |
| 5,448,214 A | 9/1995 | Laskaris | |
| 5,474,069 A | 12/1995 | Wong et al. | |
| 5,500,596 A | 3/1996 | Grist et al. | |
| 5,619,996 A | 4/1997 | Beresten | |
| 5,801,609 A | 9/1998 | Laskaris et al. | |
| 5,914,600 A * | 6/1999 | Pulyer ........................... | 324/319 |
| 5,929,639 A | 7/1999 | Doty | |
| 5,939,962 A | 8/1999 | Tahara et al. | |
| 6,137,291 A | 10/2000 | Szumowski et al. | |
| 6,163,154 A * | 12/2000 | Anderson et al. ............. | 324/320 |
| 6,241,669 B1 | 6/2001 | Furuta et al. | |
| 6,249,121 B1 | 6/2001 | Boskamp et al. | |

(Continued)

*Primary Examiner* — Brij Shrivastav
(74) *Attorney, Agent, or Firm* — Polsinelli Shughart PC; Teddy C. Scott, Jr.

(57) ABSTRACT

An apparatus for imaging includes: a main magnet to generate a substantially uniform main $B_0$ magnetic field through an examination region; and a coil system including a first coil layer and a second coil layer disposed substantially parallel to the first coil layer with a defined air gap in a radial direction, the first coil layer including a first coil array, the second coil layer including a second coil array, the first and second coil arrays being coupled and cooperating to selectively produce a prespecified $B_1$ magnetic field within the examination region.

23 Claims, 9 Drawing Sheets
(6 of 9 Drawing Sheet(s) Filed in Color)

U.S. PATENT DOCUMENTS

| | | |
|---|---|---|
| 6,317,619 B1 | 11/2001 | Boernert et al. |
| 6,404,197 B1 * | 6/2002 | Anderson et al. ............. 324/311 |
| 6,867,593 B2 | 3/2005 | Menon et al. |
| 6,906,518 B2 | 6/2005 | Leussler |
| 6,946,840 B1 | 9/2005 | Zou et al. |
| 6,952,100 B1 | 10/2005 | McKinnon et al. |
| 7,012,430 B2 * | 3/2006 | Misic ............................ 324/318 |
| 7,221,160 B2 * | 5/2007 | Leussler et al. ............... 324/318 |
| 7,646,274 B2 * | 1/2010 | Rapoport ...................... 335/296 |
| 2005/0059882 A1 | 3/2005 | Tropp |
| 2005/0065431 A1 | 3/2005 | Reiderman et al. |
| 2006/0061360 A1 | 3/2006 | Leussler et al. |
| 2010/0033186 A1 * | 2/2010 | Overweg et al. .............. 324/318 |
| 2010/0259110 A1 * | 10/2010 | Kurs et al. ..................... 307/104 |
| 2011/0172518 A1 * | 7/2011 | Rapoport ...................... 600/422 |

\* cited by examiner

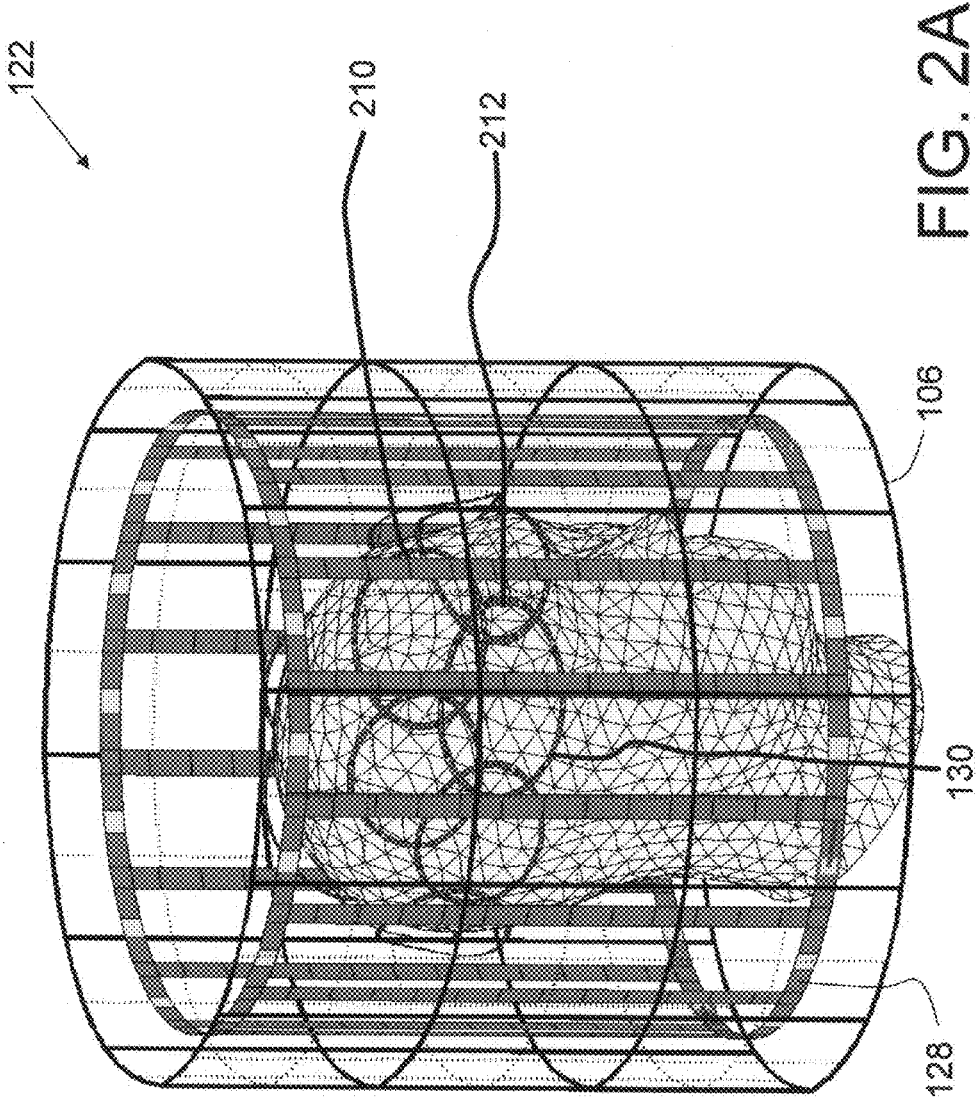

TRANSMIT PROFILE CONTROL IN MRI

CROSS-REFERENCE TO RELATED PATENT APPLICATIONS

This application is a national stage application of PCT International Patent Application No. PCT/US2008/001911 filed on Feb. 13, 2008 and claims the priority of the U.S. Provisional Application No. 60/900,972 filed on Feb. 13, 2007, the subject matter of each above-mentioned application is herein being incorporated by reference in its entirety.

BACKGROUND

The following relates to the magnetic resonance arts. It finds particular application in high field magnetic resonance imaging, at, for example, approximately 3 Tesla or higher, and will be described with particular reference thereto. However, it also finds application in magnetic resonance imaging or spectroscopy performed at lower magnetic fields, and in the like applications which may benefit from a controlled $B_1$ magnetic field.

In magnetic resonance imaging (MRI), an imaging subject is placed in a temporally constant main $B_0$ magnetic field and subjected to radio frequency (RF) excitation pulses to generate nuclear magnetic resonances in the imaging subject. Magnetic field gradients are superimposed on the main $B_0$ magnetic field to spatially encode the magnetic resonances. The spatially encoded magnetic resonances are read out and reconstructed based on the spatial encoding to generate magnetic resonance images.

Typically, RF coils are used for transmit and receive modes. In the transmit mode, RF coils generate a $B_1$ magnetic field that excites nuclear spins from low-energy states to high-energy states at the corresponding Larmor Frequency. In the receive mode, the same set or a different set of RF coils detect the echo generated by nuclear spins that transit from high-energy states to low-energy states. In the transmit mode, RF coils are expected to provide the desired excitation, e.g., a $B_1$ magnetic field profile for a given imaging method. However, at the higher main $B_0$ magnetic fields, such as at approximately 3 Tesla or higher. For example, when the imaging is performed at 7 Tesla, the resonant or Larmor frequency of $^1H$ shifts into the very high frequency (VHF) or ultra high frequency (UHF) domain. Electrodynamic material properties of the imaged subject, such as electric conductivity and dielectric permittivity increasingly distort the transmitted $B_1$ magnetic field. These distortions are typically subject-dependent, and may also depend upon the positioning of the imaging subject, the region of interest and distribution of macroscopic fractions with different electrodynamic material properties within the subject that is being imaged. For example, dynamic reordering/redistribution of dielectric properties (heart/lung placement, -size, -shape) may occur which needs to be addressed within the whole body in vivo investigation.

At higher magnetic field strengths, the axial dimension of the region of interest (ROI) is comparable to or larger than a wavelength. The sinusoidal or the co-sinusoidal current distribution provided by the first Fourier mode does not generate a homogeneous field inside such a finite-length ROI. The phase variation in the transverse dimension becomes large and hot spots appear at the phantom center due to the so-called dielectric resonance effect.

Several methods have been proposed to improve high-field $B_1$ magnetic field homogeneity. One approach seeks closer approximations of boundary current distributions with respect to a finite-length ROI. The approximation is implemented by distributed circuitry.

Another approach to improve the homogeneity of $B_1$ magnetic field is to actively control the phase and magnitude of the transmit signal, for example, with a phased-array transmit coil. However, due to the axial invariance of most phased-array structures, it is typically found that $B_1$ homogeneity may only be optimally achievable on one axial slice for one phase-magnitude configuration.

Another approach to improve the homogeneity of $B_1$ magnetic field is to use shimming by inserting high-permittivity material. More specifically, for non traveling-wave coils, where subjects are treated as dielectric resonators, the equivalent ROI radius is increased by inserting high-permittivity material; thus, the $B_1$ magnetic field homogeneity is accordingly improved.

Yet, some MRI applications require localized $B_1$ magnetic field excitations. The localized $B_1$ magnetic field excitations have the advantage of reduced specific absorption rate (SAR) and thus improved patient safety. For example, in some arterial spin labeled (ASL) perfusion MRI, RF coils are used to saturate the proton spins in the common carotid arterial. In in-vivo spectroscopic MR imaging, spins in a specific region are selectively excited.

BRIEF DESCRIPTION

One embodiment includes a magnetic resonance imaging apparatus, comprising: a main magnet to generate a substantially uniform main $B_0$ magnetic field through an examination region; a coil system including a first coil layer and a second coil layer disposed substantially parallel to the first coil layer with a defined air gap in a radial direction, the first coil layer including a first coil array, the second coil layer including a second coil array, the first and second coil arrays being coupled and cooperating to selectively produce a prespecified $B_1$ magnetic field within the examination region.

One embodiment includes a magnetic resonance imaging method, comprising: generating a substantially uniform main $B_0$ magnetic field through an examination region; and generating a prespecified $B_1$ magnetic field within the examination region.

One embodiment includes a coil arrangement, comprising: a first coil layer including a first coil array; and a second coil layer including a second coil array, the second coil layer being disposed substantially parallel to the first coil layer with a defined air gap in a radial direction, the first and second coil arrays being coupled and cooperating to selectively produce a prespecified $B_1$ magnetic field within an examination region.

BRIEF DESCRIPTION OF THE DRAWINGS

The foregoing and other features of various embodiments of the invention will be apparent from the following, more particular description of such embodiments of the invention, as illustrated in the accompanying drawings, wherein like reference numbers generally indicate identical, functionally similar, and/or structurally similar elements. The left-most digit in the corresponding reference number indicates the drawing in which an element first appears.

This patent or application file contains at least one drawing executed in color. Copies of this patent or patent application publication with color drawing(s) will be provided by the Office upon request and payment of the necessary fee.

FIG. 2A diagrammatically illustrates an exemplary coil arrangement according to an exemplary embodiment of the invention;

DETAILED DESCRIPTION

Exemplary embodiments are discussed in detail below. While specific exemplary embodiments are discussed, it should be understood that this is done for illustration purposes only. In describing and illustrating the exemplary embodiments, specific terminology is employed for the sake of clarity. However, the invention is not intended to be limited to the specific terminology so selected. A person skilled in the relevant art will recognize that other components and configurations may be used without parting from the spirit and scope of the invention. It is to be understood that each specific element includes all technical equivalents that operate in a similar manner to accomplish a similar purpose. Each reference cited herein is incorporated by reference. The examples and embodiments described herein are non-limiting examples.

Figure 1A:
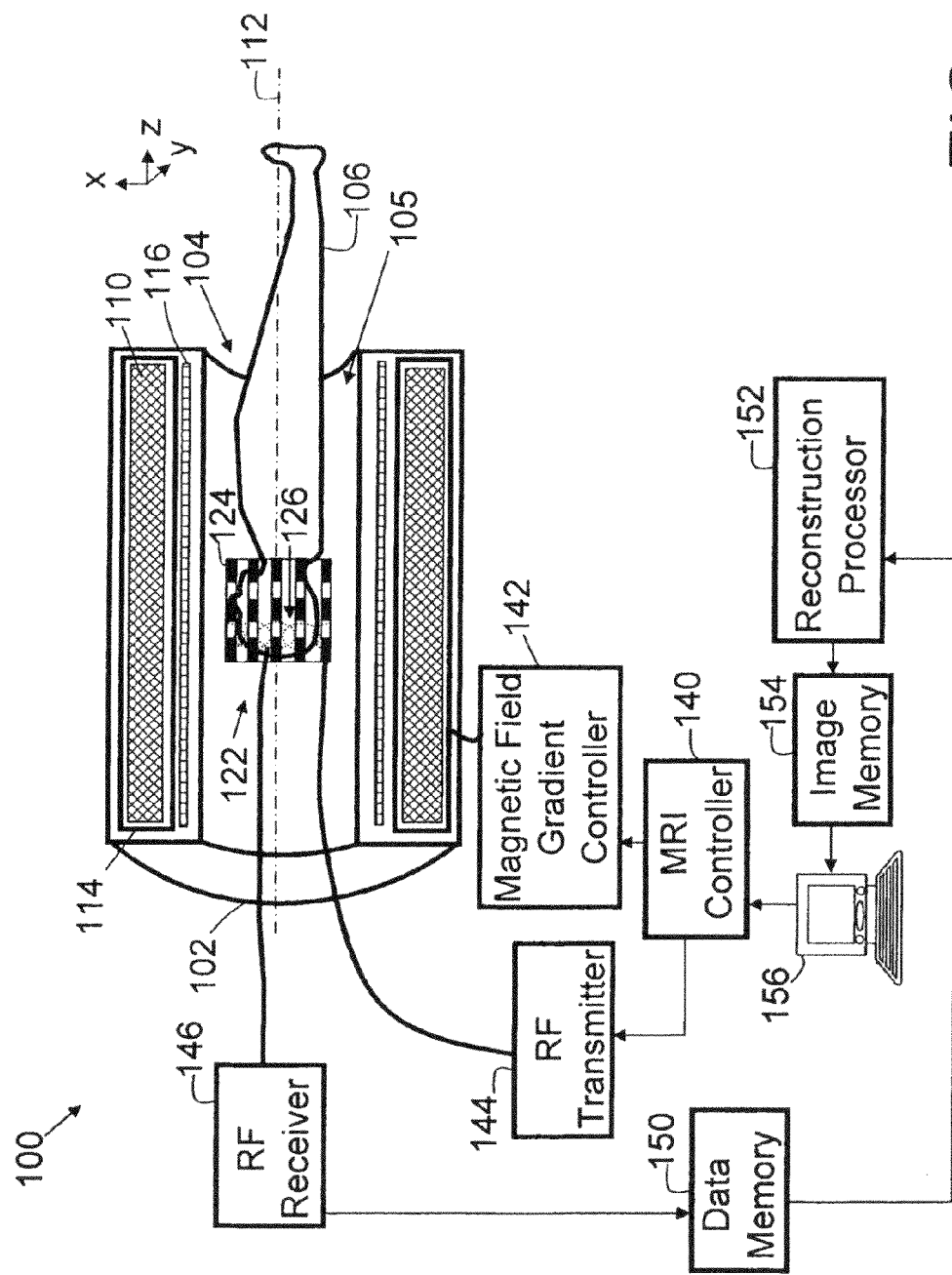
FIG. 1A diagrammatically illustrates an exemplary magnetic resonance imaging system according to an exemplary embodiment of the invention.

With reference to FIG. 1A, a magnetic resonance imaging scanner or system 100 may include a housing 102 defining a generally cylindrical scanner bore 104 defining an examination region 105, inside of which an associated imaging subject 106 is disposed. In FIG. 1A, the housing 102 is shown in cross-section to illustrate the inside of the housing 102. Main magnetic field coils 110 may be disposed inside the housing 102, and may produce a main $B_0$ magnetic field parallel to a central axis 112 of the scanner bore 104. In FIG. 1A, the direction of the main $B_0$ magnetic field is parallel to the z-axis of the reference x-y-z Cartesian coordinate system. Main magnetic field coils 110 are typically superconducting coils disposed inside cryoshrouding 114, although resistive main magnets may also be used. The main magnetic field coils 110 may generate the main $B_0$ magnetic field, at approximately 3 Tesla or higher, which may be substantially uniform in an imaging volume of the bore 104.

The housing 102 also houses or supports magnetic field gradient coil(s) 116 for selectively producing known magnetic field gradients parallel to the central axis 112 of the bore 104, along in-plane directions transverse to the central axis 112, or along other selected directions. In one embodiment, the gradient coil(s) 116 are shielded with shielding coil(s) (not shown). The shielding coils are designed to cooperate with the gradient coil 116 to generate a magnetic field which has a substantially zero magnetic flux density outside an area defined by the outer radius of the shielding coil(s).

The magnetic resonance imaging scanner 100 may include a radio frequency coil arrangement or system 122 to selectively excite and/or detect magnetic resonances. The radio frequency coil arrangement 122 is disposed inside the bore 104 and may include first or outer coil layer 124 and second or inner coil layer 126 extending substantially parallel to one another with a defined air gap in a radial direction y. Although only one inner coil layer 126 is illustrated, a number of inner coil layers may be, for example, two, three, four, . . . , ten or more layers, disposed substantially parallel to one another with defined air gaps in the radial direction y.

Figure 1B:
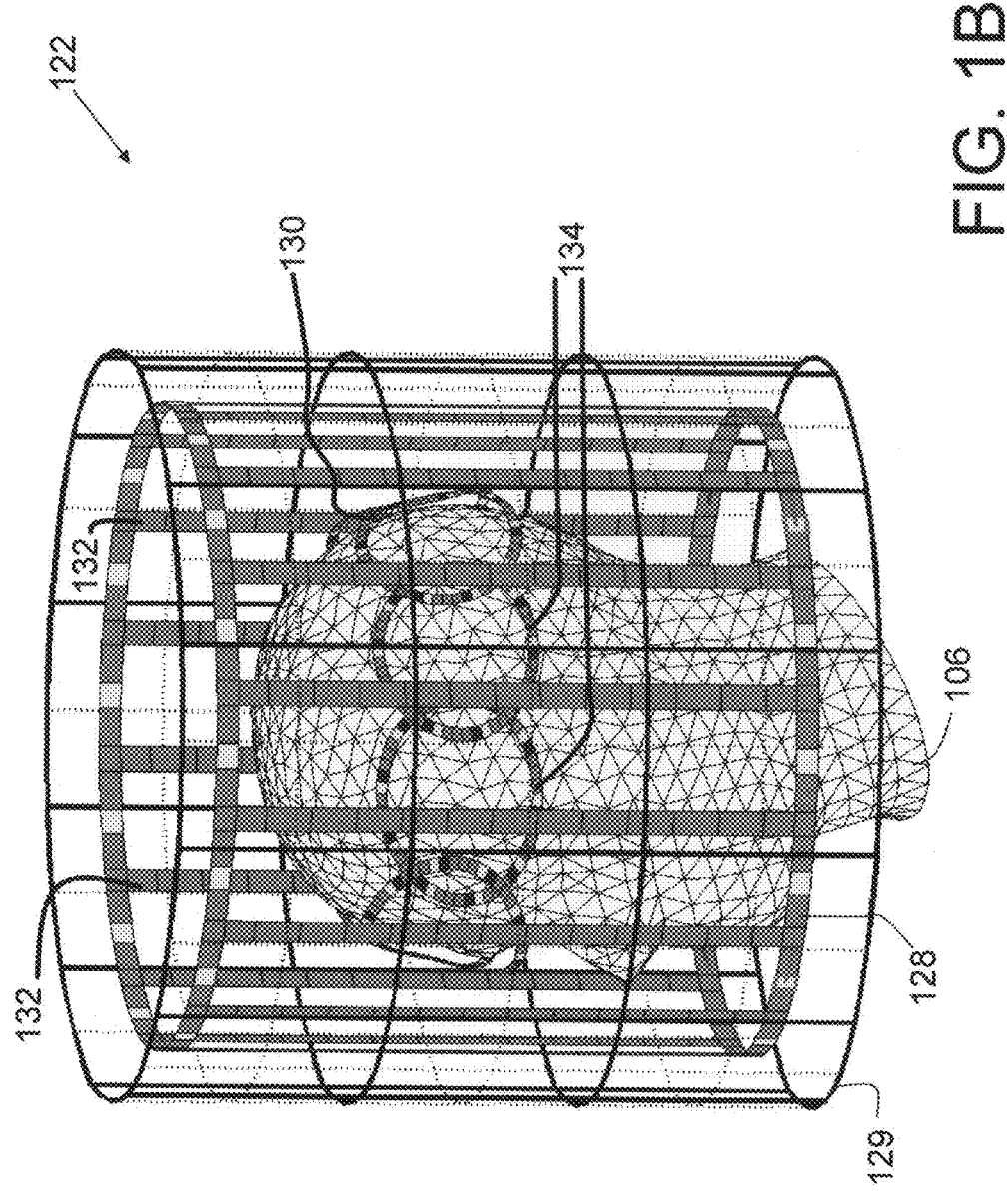
FIG. 1B diagrammatically illustrates an exemplary coil arrangement according to an exemplary embodiment of the invention.

With continuing reference to FIG. 1A and further reference to FIG. 1B, the outer coil layer 124 includes one or more outer layer coil arrays 128 surrounded by a shield 129. Each outer layer coil array 128 may include a plurality of coil elements or coils 132. The inner coil layer 126 includes one or more coil arrays 130 including a plurality of coil elements or coils 134. For example, the coil arrangement 122 may be used to image a brain (as illustrated), a heart, a leg, a body part, or the like. As explained in a greater detail below, the coil arrays 128, 130 of the outer and inner coil layers 124, 126 cooperate to transmit a selected $B_1$ magnetic field, such as, for example, a uniform $B_1$ magnetic field or a non-uniform $B_1$ magnetic field.

The inner coil layer 126 may include receive coils or elements. Alternatively, the magnetic resonances may be both excited and received by a single coil array, such as, for example, by the outer layer coil array 128. It will be appreciated that if the outer layer coil array 128 is used for both transmitting and receiving, then the inner layer coil array 130 is optionally omitted.

An MRI controller 140 operates magnetic field gradient controller or controllers 142 and a radio frequency transmitter or transmitters 144 coupled to the outer layer coil array 128 to selectively energize the outer layer radio frequency coil array 128. A baseline, primary or first $B_1^I$ magnetic field may be generated. A secondary or second $B_1^{II}$ magnetic field, generated by the inner coil array 130, may be superimposed on the baseline $B_1^I$ magnetic field to provide the $B_1$ magnetic field of a desired profile. In one embodiment, the outer layer coil array 128 is quadrature driven.

Magnetic resonance is generated and spatially encoded in at least a portion of a region of interest of the imaging subject 106. By applying selected magnetic field gradients via the gradient coils 116, a selected k-space trajectory is traversed, such as a Cartesian trajectory, a plurality of radial trajectories, or a spiral trajectory. Alternatively, imaging data may be acquired as projections along selected magnetic field gradient directions. During imaging data acquisition, a radio frequency receiver or receivers 146 coupled to the receive elements or the coil array 128 may acquire magnetic resonance samples that are stored in a magnetic resonance data memory 150.

The imaging data may be reconstructed by a reconstruction processor 152 into an image representation. In the case of Cartesian k-space sampled data or other data resampled appropriately, a Fourier transform-based reconstruction algorithm may be employed. Other reconstruction algorithms, such as, for example, a filtered backprojection-based reconstruction, may also be used depending upon the format of the acquired magnetic resonance imaging data. For SENSE (sensitivity encoding) imaging data, the reconstruction processor 152 reconstructs folded images from the imaging data acquired by each RF coil and combines the folded images along with coil sensitivity parameters to produce an unfolded reconstructed image.

The reconstructed image generated by the reconstruction processor 152 may be stored in an image memory 154, and may be displayed on a user interface 156, stored in non-volatile memory, transmitted over a local intranet or the Internet, viewed, stored, manipulated, or so forth. The user interface 156 may also enable a radiologist, technician, or other operator of the magnetic resonance imaging scanner 100 to communicate with the magnetic resonance imaging controller 140 to select, modify, and execute magnetic resonance imaging sequences.

With continuing reference to FIGS. 1A and 1B, the coil array 128 of the outer coil layer 124 is actively driven and may include any typical coil structure that radiates the baseline $B_1^I$ magnetic field. An example of the coil array 128 of the outer coil layer 124 includes a conventional birdcage coil array 128 including parallel coil elements or rods 132. Of course, it is contemplated that the coil array 128 of the outer coil layer 124 may include surface coils or saddle coils.

The coil array 130 of the inner coil layer 126 may be coupled to the coil array 128 of the outer coil layer 124 and radiate the secondary $B_1^{II}$ magnetic field that appropriately superimposes the baseline $B_1^I$ magnetic field. The winding pattern of the inner layer coil array 130 may be determined to produce a desired target magnetic field. Because the imaging subjects 106 are not perfectly round, maps of the $B_1$ magnetic field of higher frequencies may exhibit a considerable degree of differences along the azimuthal direction. In one embodiment, the coils 134 of the inner coil layer 126 interact with the baseline $B_1^I$ magnetic field differently at different azimuthal locations. For example, the inner coil layer 126 includes azimuthally distributed surface coils 134. In the distributed coils arrangement, the distributed coils are positioned spaced over a surface so that a sum of centroid positions represents the desired harmonic. Distributed coils may assist in correcting patient induced inhomogeneity of the $B_1$ magnetic field.

In one embodiment, at least one of the outer or inner coil layer 124, 126 includes an array of surface coils. The coil elements 132, 134 of the outer and inner coil layers 124, 126 may include electrical and/or magnetic dipoles, e.g., striplines and/or loop coils. The pattern for the coils may be selected based on the design considerations. The examples of the layouts for the loop coils include overlapped loop coils, gapped loop coils, and touched neighboring loop coils. Generally, to form the outer or inner coil layer 124, 126, any number of coil arrays 128, 130 with any number of coil elements 132, 134 may be used. For example, for a localized $B_1$ magnetic field profile, a single coil array 130 may be used in the inner coil layer 126. Generally, increasing the number of coil arrays 130 and/or coil elements 134 of the inner coil layer 126 introduces more degrees of freedom that may be engineered to achieve a globally homogenized $B_1$ magnetic field profile or an arbitrary in-homogeneous $B_1$ magnetic field profile. In the exemplary embodiments of FIGS. 1A and 1B, a single inner coil array 130 including eight coil elements 134 is shown for illustrative purposes.

The coil arrays 130 of the inner coil layer 126 may be disposed on a former (not shown), which may be manufactured from fiber glass. The former may be disposed with a defined air gap from the imaging subject 106. The air gap is selected for maximum patient comfort and allows for installation of the electronics, such as a separate MRI receive coil array. The air gap can not be selected too great as the electromagnetic fields re-radiated from the coil array 130 of the inner layer 126 may decay rapidly in the vicinity of inner coil layer 126 resulting in the magnetic field patterns which are less azimuthally distinguishable.

Besides choosing the appropriate type, number and layout of the inner layer coil elements 134, another consideration is selective modification of the magnitude and/or the phase of the $B_1^{II}$ secondary magnetic field.

Generally, a loop coil may be viewed in a simplified circuit model as a series RLC network powered by an electro-dynamic voltage. The induced coil currents intensity is proportional to the electro-dynamic voltage and inverse proportional to the series RLC network impedance. The voltage is provided by the baseline electromagnetic field according to Faraday's law, which states that the electro-dynamic voltage is proportional to the rate of the magnetic flux changes with respect to time. The magnetic flux is proportional to the magnetic field strength, e.g., B field, and the projection of the area of a loop coil on the direction of the B field. For example, the secondary $B_1^{II}$ magnetic field may be modified by changing the RLC network impedance. For example, the secondary $B_1^{II}$ magnetic field may be modified by using resistive attenuation, frequency detuning, a combination of the resistive attenuation and frequency detuning, or angled positioning with respect to the outer layer transmit coil.

Resistive attenuation may be achieved by connecting resistive components in series to the inner layer coil 134. This corresponds to increasing the resistance R in the coil system 122. Thus, the induced current density decreases. In frequency detuning; each inner layer coil 134 is individually tuned to a frequency different from the Larmor frequency, e.g., the resonant frequency of the outer layer coil array 128, by using at least one of capacitors, inductors, or a combination of the capacitors and inductors. Each method, respectively, corresponds to changing the capacitance C, the inductance L, or both the capacitance C and inductance L in the coil system 122. In one embodiment, the frequency detuning is achieved by using capacitors available in the loop coil design. Since the impedance of a coil element achieves its minimum at the resonance frequency, frequency detuning increases the coil impedance when imaging at the Larmor frequency. The induced current intensity is reduced. In one embodiment, the detuning capacitors and inductors are used to afford more freedom in design. In one embodiment, the resistance or capacitance is changed remotely so that the amount of coupling is optimized for each individual sample, for example, different imaging subjects 106.

For example, a loop coil tuned at the Larmor frequency is used as the reference. Applying extra capacitance to detune the coil is equivalent to a geometrical change of decreasing the circumference of the loop coil. On the other hand, applying extra inductance to detune the coil is equivalent to a geometrical change of increasing the circumference of the loop coil. Thus, the geometrical features or their equivalents may be changed to control the induced current intensity.

Figure 1C:
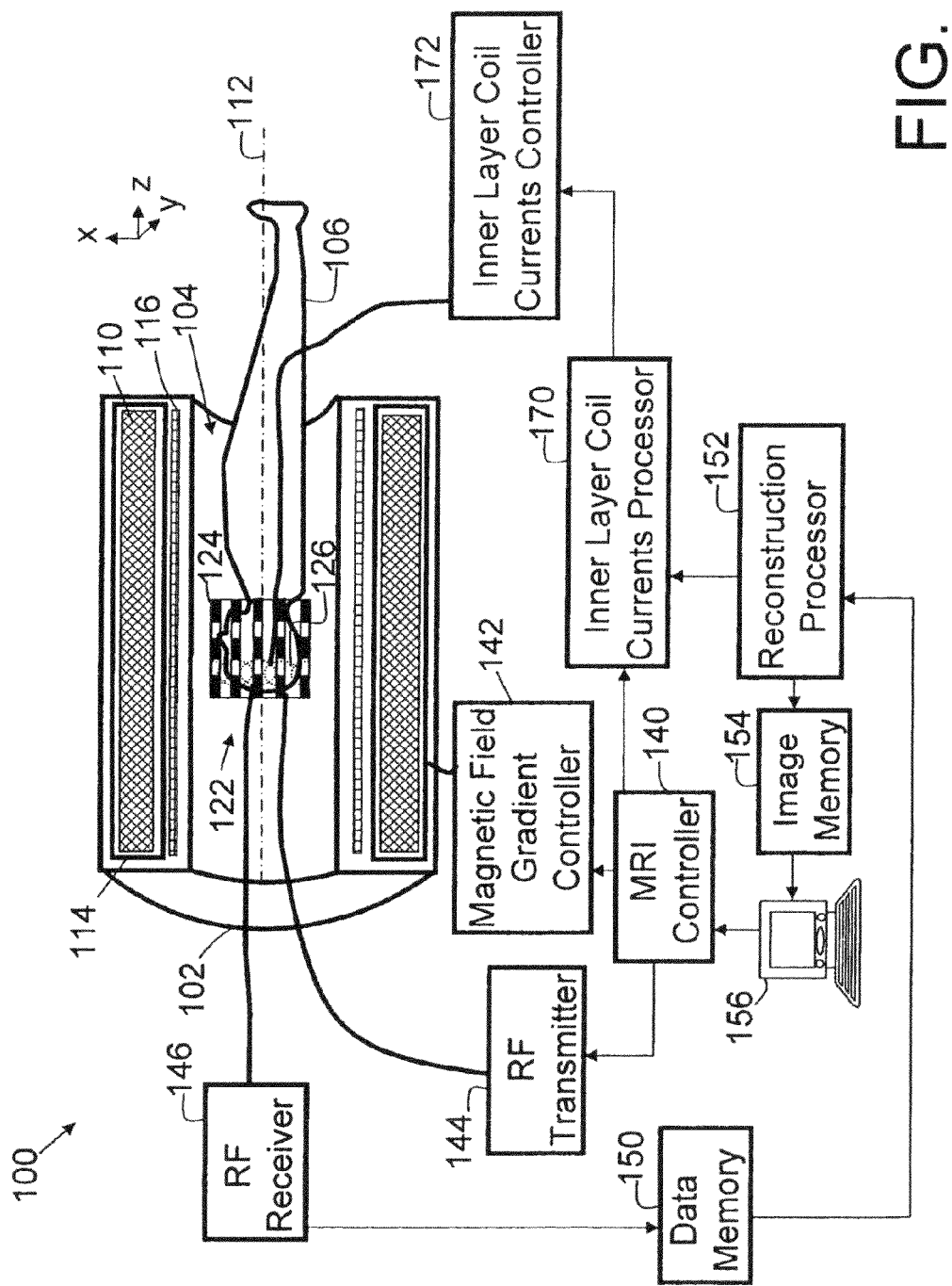
FIG. 1C diagrammatically illustrates an exemplary magnetic resonance imaging system according to an exemplary embodiment of the invention.

With continuing reference to FIG. 1B and further reference to FIG. 1C, each inner layer coil 134 produces a magnetic field distribution within the bore 104. In this exemplary embodiment, an inner layer coil currents processor 170 may determine appropriate currents for one or more of the inner layer coils 134 to reduce distortions in the baseline $B_1^I$ magnetic field. The currents processor 170 may select appropriate currents based on known configurations of the inner layer coils 134 and on the information of the magnetic field non-uniformity that needs to be corrected. Non-uniformity of the baseline $B_1^I$ magnetic field may be determined in various ways, such as, for example, by acquiring a magnetic field map using a magnetic field mapping magnetic resonance sequence executed by the scanner 100, by reading optional magnetic field sensors (not shown) disposed in the bore 104, by performing a priori computation of the expected magnetic field distortion produced by introduction of the imaging subject 106, or so forth. Magnetic field measurement sequences may be intermixed with the imaging sequence to check the baseline $B_1$ magnetic field magnitude periodically, e.g. after each slice or batch of slices. The currents processor 170 may control an inner layer coil controller 172 to energize one or more of the inner layer coils 134 at the selected currents. Dynamic, i.e., pulsed, control of the coil current settings is contemplated. In one embodiment, the inner layer coils 134 are switched between slices or batches of slices. Of course, it is contemplated that the inner coil array 130 may be driven by a constant current source.

In one embodiment, in which electrical dipoles are used for the coils 134 of the inner coil layer 126, the various kinds of dipole impedance modification methods, which include, for example, using resistors, capacitors, inductors or combinations of resistors, capacitors, and inductors may be applied.

With reference again to FIG. 1A and further reference to FIG. 2A, the coil arrays 130 of the inner coil layer 126 may be arranged in first and second levels 210, 212 in the axial direction z. In one embodiment, in which the region of interest (ROI) has a large span in the axial direction z at higher frequencies, the coil arrays 130 of the inner coil layer 126 may be arranged into multiple levels. The coil elements 134 of the coil arrays 130 of the inner coil layer 126 may have various arrangements. For example, the coil elements 134 of each level 210, 212 of the coil arrays 130 may be arranged in a ring in which the coil elements 134 overlap at the same level and between the first and second levels 210, 212.

Each level or ring 210, 212 of coil elements may be laid out according to design considerations. For example, if electrical dipoles are used for the coil array 130 of the inner coil layer 126, the coil elements 134 may be gapped or clustered. The clustered dipoles may form any pattern. An example of dipole clusters includes crosses formed by two dipoles that are orthogonal to one another. Other patterns are also contemplated.

Figure 2B:
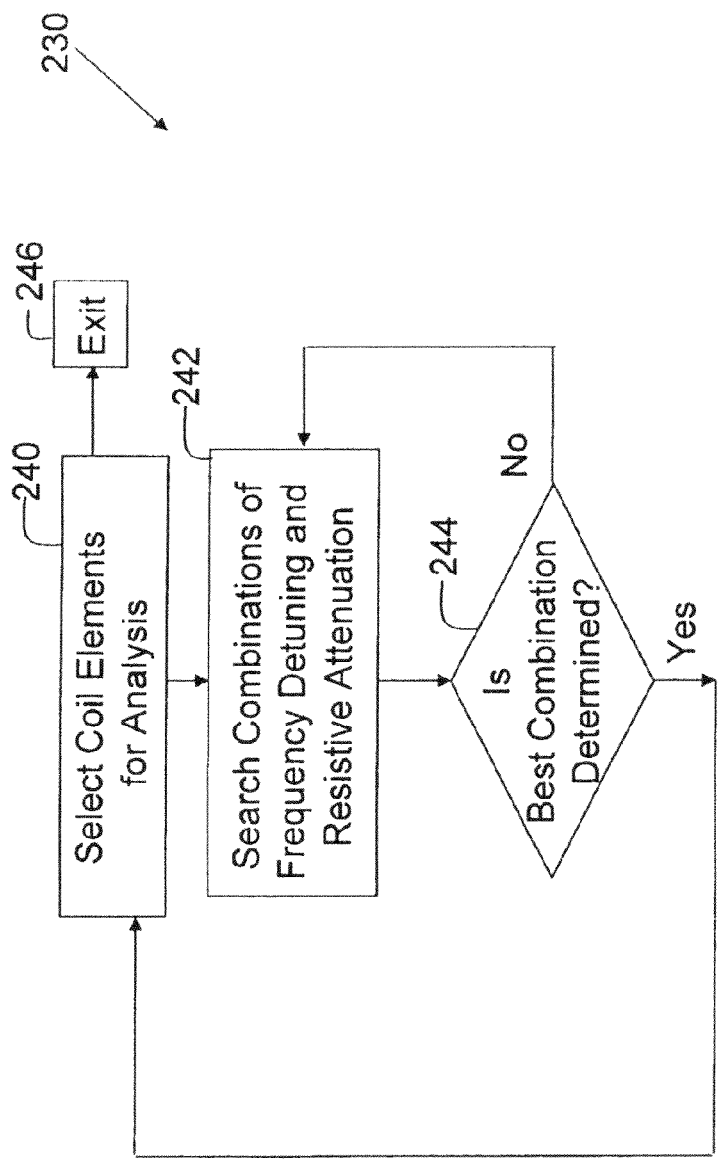
FIG. 2B illustrates an exemplary flow chart for coupling optimization according to an exemplary embodiment of the invention.

With continuing reference to FIG. 1A and further reference to FIG. 2B, each coil element 132, 134 includes electronic circuitry to provide an appropriate coupling between the outer and inner coil layers 124, 126. The amount of coupling required for each inner layer coil element 134 may be determined by a coupling process 230 which may use a full-wave numerical approach. In the process 230, the combination of frequency detuning and resistive attenuation may be used to scale the power down appropriately. The numerical approach may apply, for example, the method of moments estimation, known in the art, with the presence of the imaging subject 106.

In block 240 of the process 230, the method of moments estimation may start with the analysis of selected individual coil elements, for example, four individual non-overlapping elements. In block 242, all combinations of frequency detuning and resistive attenuation for the best local B magnetic field homogeneity performance may be searched. If, in block 244, it is determined that the best combination of the coupling elements is not found, the flow proceeds to the block 242. If, in block 244, it is determined that the best combination of the coupling elements is found, then the flow proceeds to the block 240 and additional coil elements may be added to the analysis. For example, the coupling of other four elements that overlap with the previous group of four elements is optimized based on a pre-selected criterion with the presence of their nearest neighbors, which now take the optimized frequency detuning and resistive attenuation. Again, an exhaustive search may be applied to find the best global homogeneity performance in a large range of axial slices. The flow may exit 246 the process 230 from block 240 once the optimal coupling of all coil elements is determined. In one embodiment, the first round of optimization finishes once the initial coupling of all eight elements is determined. Another round of optimization is possible after the first round. The results typically converge after at two rounds of optimizations. Such strategy belongs to multi-directional optimization schemes. Any advanced method in that category, such as Powell's method, may also be used.

Figure 3A:
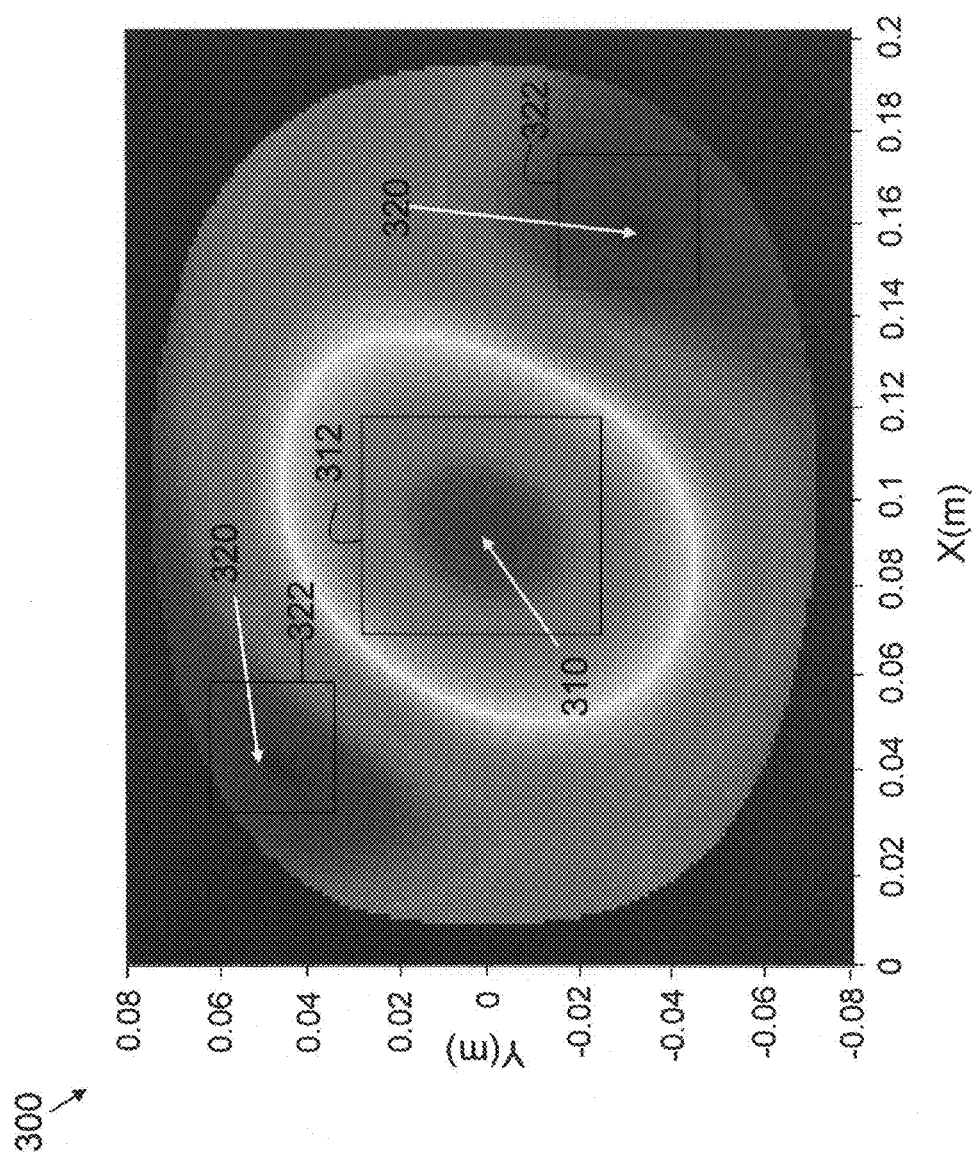
FIG. 3A illustrates an exemplary $B_1$ magnetic field map.

With reference to FIG. 3A, a $B_1$ magnetic field map 300 of the conventional 32-element shielded birdcage coil on an axial slice that needs to be homogenized is illustrated. As shown, the profile 300 includes a local maxima 310 disposed about a center area 312 of the region of interest. Local minima 320 are disposed about peripheral regions 322. The inhomogeneous pattern in the peripheral regions 322 is not uniform in the azimuthal direction.

Figure 3B:
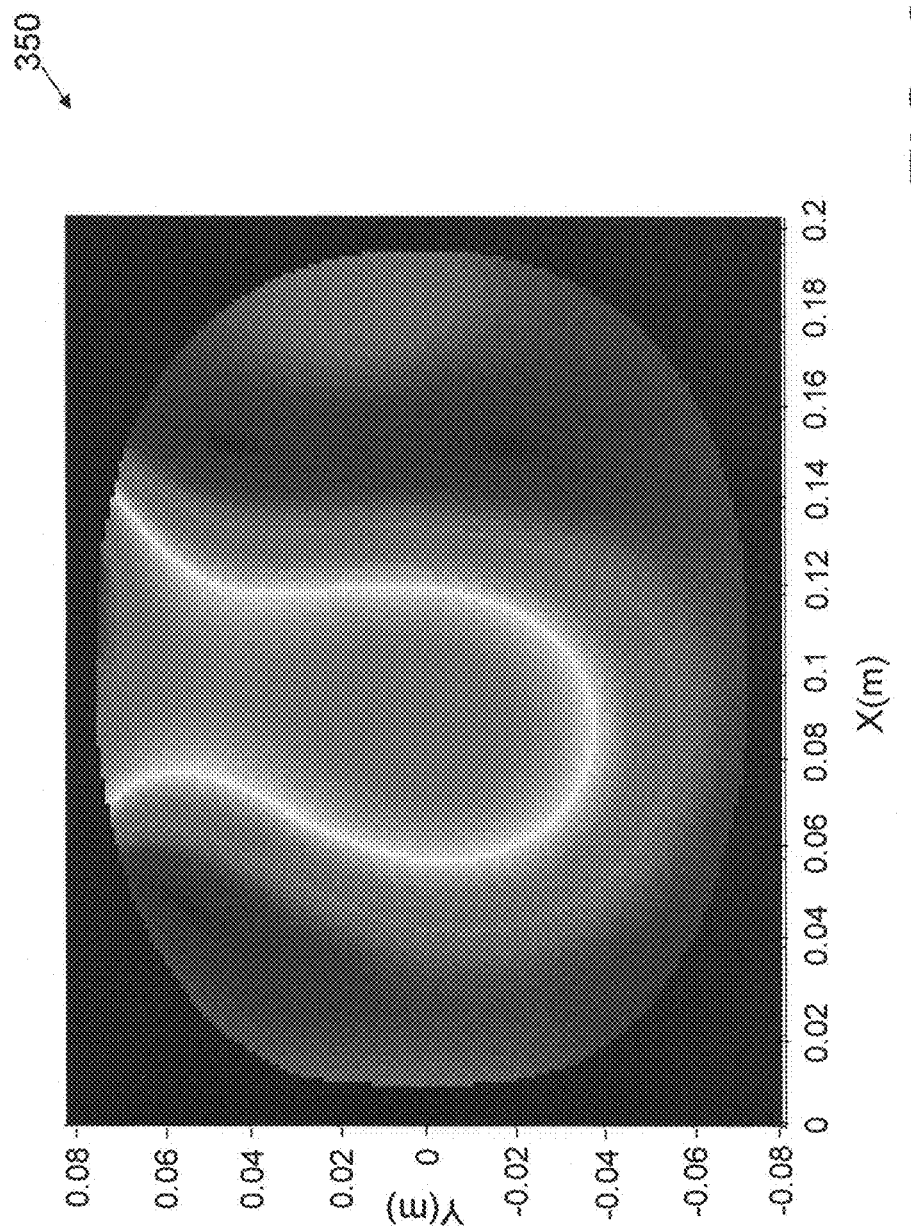
FIG. 3B illustrates an exemplary $B_1$ magnetic field map of FIG. 3A corrected with a single inner layer coil according to an exemplary embodiment of the invention.

With reference to FIG. 3B, a corrected $B_1$ magnetic field map 350 of the conventional 32-element shielded birdcage coil of FIG. 3A is illustrated. The secondary $B_1^{II}$ magnetic field generated by the inner layer coil array 130 is superimposed on the profile 300. For the inner layer coil array 130, a single inner layer coil element 134 is used to provide the secondary $B_1^{II}$ magnetic field excitation. Compared to FIG. 3A, the local homogeneity of the $B_1$ magnetic field is improved at the azimuthal location corresponding to the position of the coil element 134.

Figure 4:
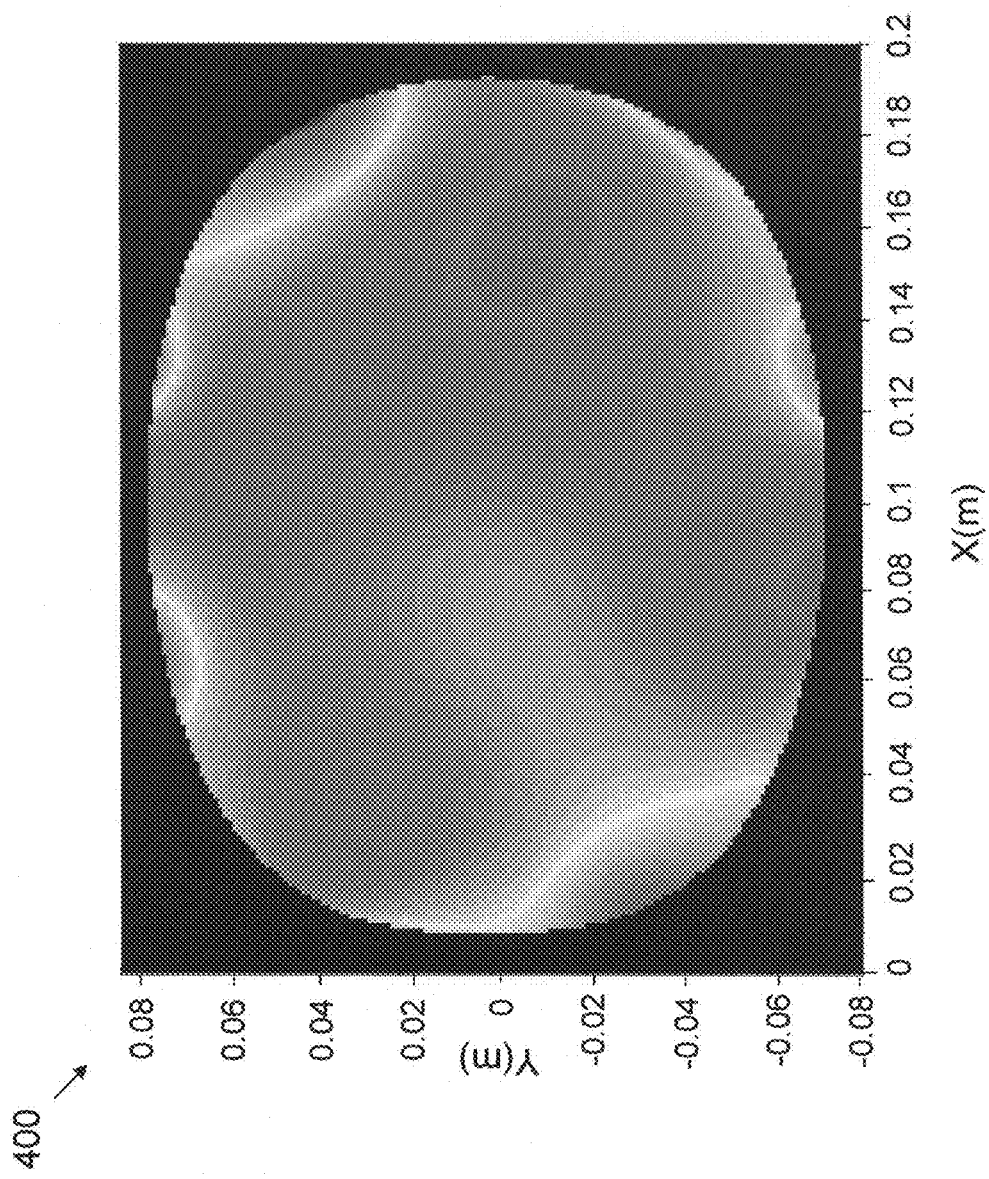
FIG. 4 illustrates an exemplary $B_1$ magnetic field map of FIG. 3A corrected with an exemplary eight element inner coil array according to an exemplary embodiment of the invention.

With reference to FIG. 4, a substantially homogenized $B_1$ magnetic field map 400 of the conventional 32-element shielded birdcage coil of FIGS. 3A and 3B is illustrated. The secondary $B_1^{II}$ magnetic field generated by the inner layer coils 134 is superimposed on the profile 300. For the inner layer coil array 130, a single-level eight-element overlapped oval coil array 130 is used to provide the secondary $B_1^{II}$ magnetic field excitation. In one embodiment, the capacitive coupling between the nearest neighbors for the overlapped loop coils 134 is substantially reduced or absent.

Figure 5:
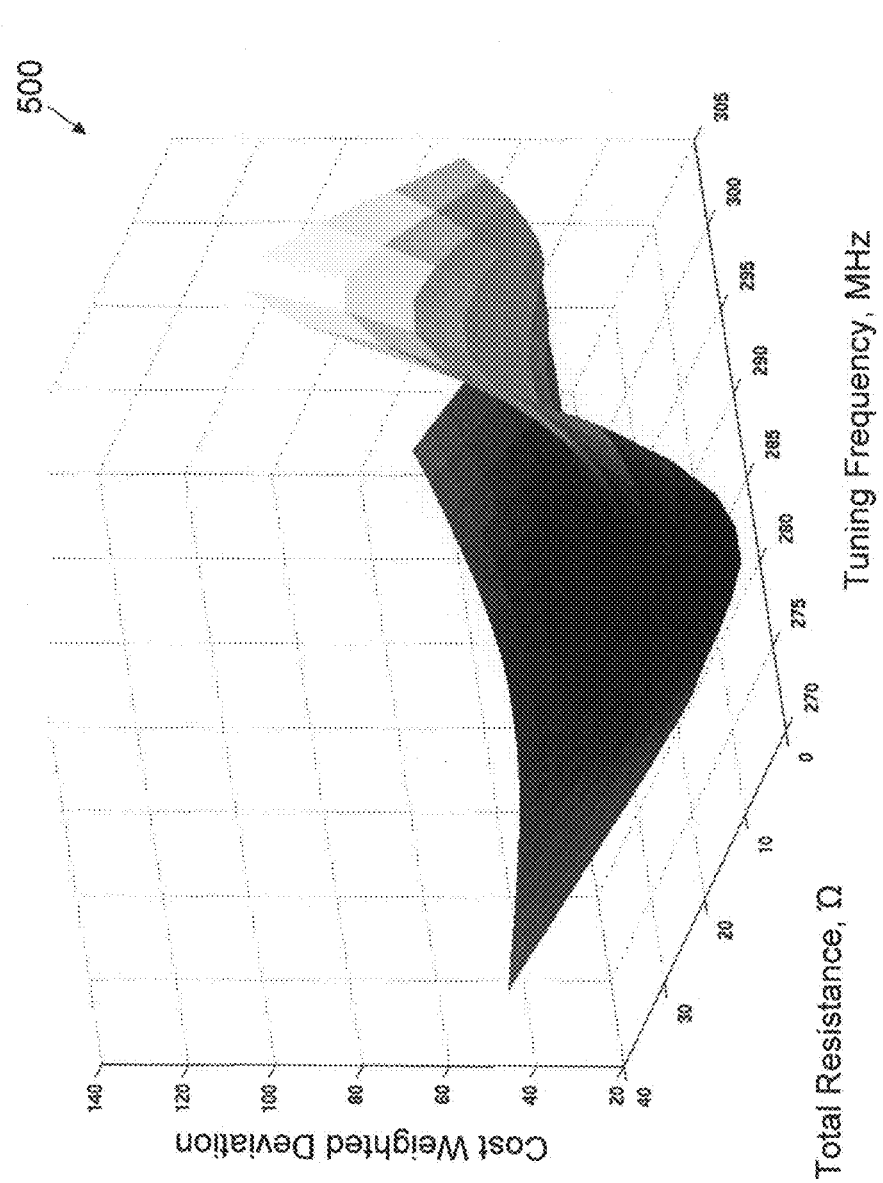
FIG. 5 illustrates exemplary optimization results of a single coil element of FIG. 3B according to an exemplary embodiment of the invention.

With reference to FIG. 5, optimization results 500 of a single coil element of FIG. 3B are shown. For example, the cost weighted deviation represents a measure of $B_1$ magnetic field inhomogeneity across several axial slices. Thus, low cost implies higher degree of $B_1$ magnetic field homogeneity. Low cost may be achieved either by resistive attenuation at a fixed resonant frequency, by frequency detuning with no resistive attenuation, or by a combination of resistive attenuation and frequency detuning.

As shown, the cost changes smoothly, not drastically, in the vicinity of the lowest cost point. Since the resonant frequency of loop coils changes only slightly with respect to small imaging subjects, the above observation indicates that if the inner layer coil array 130 is optimized with respect to one small imaging subject, its performance may still be acceptable to other small imaging subjects. Thus, exemplary embodiments described above may be simplified as the coil array 130 of the inner coil layer 126 does not need to be designed with respect to specific subjects.

The invention is described in detail with respect to exemplary embodiments, and it will now be apparent from the foregoing to those skilled in the art that changes and modifications may be made without departing from the invention in its broader aspects, and the invention, therefore, as defined in the claims is intended to cover all such changes and modifications as fall within the true spirit of the invention.

The invention claimed is:

1. A magnetic resonance imaging apparatus, comprising:
a main magnet to generate a substantially uniform main $B_0$ magnetic field through an examination region; and
a radio frequency coil system to:
produce a prespecified $B_1$ magnetic field within the examination region to selectively excite magnetic resonances in at least a portion of a subject within the examination region, the radio frequency coil system including:
a first coil layer comprising a first coil array to generate a primary $B_1^I$ magnetic field; and
a second coil layer comprising a second coil array to generate a secondary $B_1^{II}$ magnetic field, the second coil array being disposed substantially parallel to the first coil layer with a defined air gap in a radial direction,
the first and second coil arrays being coupled and cooperating to:
manipulate the primary $B_1^I$ magnetic field with the secondary $B_1^{II}$ magnetic field to selectively produce the prespecified $B_1$ magnetic field; and
acquire image data based on the magnetic resonances, wherein the image data is used to reconstruct an image representation of the at least a portion of the subject; and
a memory to store the image data.

2. The magnetic resonance imaging apparatus according to claim 1, wherein the first and second coil arrays cooperate to reduce inhomogeneities in the $B_1$ magnetic field caused by the subject in the examination region.

3. The magnetic resonance imaging apparatus according to claim 1, wherein the first coil array includes at least one of:
a birdcage coil;
surface coils;
a saddle coil; or
volumetric transmit coils.

4. The magnetic resonance imaging apparatus according to claim 1, wherein the second coil array includes at least one of a surface coil or stripline coils.

5. The magnetic resonance imaging apparatus according to claim 4, wherein the surface coil of the second coil array includes at least one of:
overlapped loop coils;
touching loop coils;
gapped loop coils; or
stripline coils.

6. The magnetic resonance imaging apparatus according to claim 1, wherein the second coil array includes at least one of:
a head coil; or
a body coil.

7. The magnetic resonance imaging apparatus according to claim 1, wherein the second coil array includes:
multiple coil arrays extending in an axial direction.

8. The magnetic resonance imaging apparatus according to claim 1, wherein the second coil layer further includes:
second coil layers disposed with a defined air gap and substantially parallel one another and the first coil layer in the radial direction.

9. The magnetic resonance imaging apparatus according to claim 1, wherein the second coil array includes:
coils distributed along an axial direction for a specific radio frequency magnetic field behavior.

10. A magnetic resonance imaging method, comprising:
generating, at a main magnet, a substantially uniform main $B_0$ magnetic field through an examination region;
generating a primary $B_1^I$ magnetic field at a first radio frequency coil array disposed in a first coil layer, wherein the first radio frequency coil array is actively driven;
generating a secondary $B_1^{II}$ magnetic field with a second radio frequency coil array disposed in a second coil layer, wherein the second radio frequency coil array is a passive radio frequency coil array; and
manipulating the primary $B_1^I$ magnetic field with the secondary $B_1^{II}$ magnetic field to generate a prespecified $B_1$ magnetic field within the examination region and to selectively excite magnetic resonances in at least a portion of a subject in the examination region;
acquiring image data based on the magnetic resonances excited in the at least a portion of the subject; and
processing the image data at a processor to reconstruct an image representation of the at least a portion of the subject from the image data for display.

11. The magnetic resonance imaging method according to claim 10, wherein the first radio frequency coil array includes at least one of a birdcage coil, a surface coil, or a saddle coil, and wherein the second radio frequency coil array includes a surface coil.

12. The magnetic resonance imaging method according to claim 11, wherein the surface coil of the second coil array includes at least one of:
overlapped loop coils,
touching loop coils,
gapped loop coils, or
stripline coils.

13. The magnetic resonance imaging method according to claim 11, wherein the second coil array includes:
multiple coil arrays extending in an axial direction.

14. The magnetic resonance imaging method according to claim 11, wherein the second coil array includes:
second coil arrays disposed with a defined air gap and substantially parallel one another and the first coil array in the radial direction.

15. The magnetic resonance imaging method according to claim 11, wherein the second coil array includes:
coils distributed along an axial direction for a specific magnetic field behavior.

16. The magnetic resonance imaging method according to claim 10, wherein generating the prespecified $B_1$ magnetic field includes at least one of:
reducing inhomogeneities in the $B_1$ magnetic field caused by a subject disposed in the examination region; or generating a non-uniform localized $B_1$ magnetic field.

17. A magnetic resonance imaging scanner for performing the method of claim 10.

18. A radio frequency coil arrangement for a magnetic resonance imaging apparatus having a main magnet that generates a substantially uniform main $B_0$ magnetic field through an examination region, the radio frequency coil arrangement comprising:
a first coil layer including a first coil array to generate a primary $B_1^I$ magnetic field; and
a second coil layer including a second coil array to generate a secondary $B_1^{II}$ magnetic field, the second coil layer being disposed substantially parallel to the first coil layer with a defined air gap in a radial direction, the first and second coil arrays being coupled and cooperating to:
manipulate the primary $B_1^I$ magnetic field with the secondary $B_1^{II}$ magnetic field to selectively produce a prespecified $B_1$ magnetic field within an examination region; and selectively excite magnetic resonances in at least a portion of a subject within the examination region; and acquire image data based on the magnetic resonances for storage in a memory, wherein the image data is used to reconstruct an image representation of the at least a portion of the subject.

19. The radio frequency coil arrangement according to claim 18, wherein the first and second coil arrays cooperate to selectively produce at least one of a uniform $B_1$ magnetic field or a non-uniform $B_1$ magnetic field within the examination region.

20. The radio frequency coil arrangement according to claim 18, wherein the first coil array includes at least one of a birdcage coil, surface coils, volumetric coils or a saddle coil, and the second coil array includes at least one of a surface coil or stripline coils.

21. The radio frequency coil arrangement according to claim 18, wherein the surface coil of the second coil array includes at least one of:
overlapped loop coils,
touching loop coils,
gapped loop coils, or
stripline coils.

22. The radio frequency coil arrangement according to claim 18, wherein the second coil array includes:
multiple second coil arrays extending in an axial direction.

23. The radio frequency coil arrangement according to claim 18, wherein the second coil layer includes:
second coil layers each including at least one second coil array, the second coil layers each being disposed with a defined air gap and substantially parallel one another and the first coil layer in the radial direction.

* * * * *

UNITED STATES PATENT AND TRADEMARK OFFICE
CERTIFICATE OF CORRECTION

| | | |
|---|---|---|
| PATENT NO. | : 8,125,225 B2 | Page 1 of 1 |
| APPLICATION NO. | : 12/449514 | |
| DATED | : February 28, 2012 | |
| INVENTOR(S) | : Alan P. Koretsky et al. | |

It is certified that error appears in the above-identified patent and that said Letters Patent is hereby corrected as shown below:

On title page 1, item 75, line 4, --Hellmut Merkic-- should read "Hellmut Merkle"

Signed and Sealed this
Twenty-ninth Day of May, 2012

David J. Kappos
*Director of the United States Patent and Trademark Office*